United States Patent [19]

Merkel et al.

[11] Patent Number: 5,008,180

[45] Date of Patent: Apr. 16, 1991

[54] PHOTOGRAPHIC RECORDING MATERIAL CONTAINING A CYAN DYE-FORMING COUPLER

[75] Inventors: Paul B. Merkel; David Hoke, both of Rochester, N.Y.

[73] Assignee: Eastman Kodak Company, Rochester, N.Y.

[21] Appl. No.: 474,566

[22] Filed: Feb. 2, 1990

Related U.S. Application Data

[63] Continuation-in-part of Ser. No. 335,166, Apr. 7, 1989, abandoned.

[51] Int. Cl.$^5$ ............................ G03C 1/08; G03C 7/34
[52] U.S. Cl. ...................................... 430/552; 430/553
[58] Field of Search ......................... 430/552, 553

[56] References Cited

U.S. PATENT DOCUMENTS

| | | | |
|---|---|---|---|
| 4,333,999 | 6/1982 | Lau | 430/17 |
| 4,609,619 | 9/1986 | Katoh et al. | 430/553 |
| 4,613,564 | 9/1986 | Takada et al. | 430/549 |
| 4,640,889 | 2/1987 | Komarita et al. | 430/505 |
| 4,734,358 | 3/1988 | Takada et al. | 430/550 |
| 4,775,616 | 10/1988 | Kilminster et al. | 430/552 |
| 4,849,328 | 7/1989 | Hoke et al. | 430/553 |

FOREIGN PATENT DOCUMENTS

| | | | |
|---|---|---|---|
| 3518257 | 11/1985 | Fed. Rep. of Germany | 430/553 |
| 59-121332 | 7/1884 | Japan | 430/553 |
| 01505644 | 4/1959 | Japan . | |
| 0111643 | 7/1959 | Japan . | |
| 0111644 | 11/1959 | Japan . | |
| 59-11645 | 6/1984 | Japan | 430/553 |

*Primary Examiner*—Charles L. Bowers, Jr.
*Assistant Examiner*—Jaret C. Baxter
*Attorney, Agent, or Firm*—Richard E. Knapp

[57] ABSTRACT

A photographic rocording material is disclosed which contains a phenolic cyan dye-forming coupler which has a sulfone or a modified sulfone group in the 5- position ballast moiety and a substituted acylamino group in the 2- position of the phenolic ring.

9 Claims, No Drawings

PHOTOGRAPHIC RECORDING MATERIAL CONTAINING A CYAN DYE-FORMING COUPLER

This is a continuation-in-part of U.S. application Ser. No. 335,166, filed Apr. 7, 1989, now abandoned.

The present invention relates to a photographic recording material containing a phenolic cyan dye-forming coupler. More particularly, this invention relates to a photographic recording material containing a coupler which is used to obtain a cyan dye for color photography which coupler is typically a phenol or a naphthol which yields an azomethine dye upon coupling with oxidized aromatic primary amino color developing agent.

Known cyan couplers, including those of U.S. Pat. No. 4,333,999, have highly desirable properties in that they can provide dyes of excellent purity and hues which are shifted bathochromically to the long wavelength red absorption region. Although such couplers have been widely used, further improvements in coupler reactivity and enhanced dye absorption continue to be sought. For example, it has been difficult to obtain, with the same coupler, a dye having both high density and high coupling effectiveness. A cyan coupler yielding enhanced dye density would allow use of less image coupler in a layer. This would provide enhanced cost savings as well as image sharpness improvements. Coupling effectiveness is measured by comparing the gamma or Dmax of the resulting dye image sensitometric test curve with that of a control coupler under identical conditions.

The presence of sulfone (—$SO_2$—) groups in ballast moieties of cyan coupler compounds has been described in various publications. These publications include Japanese Patent Publication Nos. 105644/1984 (priority of Dec. 10, 1982), 111643/1984 and 111644/1984 (both having priorities of Dec. 17, 1982). Couplers having sulfone groups in the ballast moiety are also disclosed in U.S. Pat. Nos. 4,609,619 and 4,775,616 and cyan couplers having modified sulfone groups, that is groups comprising —$OSO_2$— or —$NHSO_2$— moieties, are described in U.S. Pat. No. 4,849,328.

A highly desirable property of cyan dye-forming couplers is an ability to provide acceptable dye density while at the same time providing dyes having the desired hue and saturation.

The present invention provides a photographic recording material comprising a support and a photosensitive silver halide emulsion which has associated therewith a cyan dye-forming coupler compound having the structural formula:

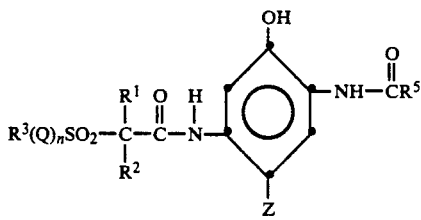

wherein:
$R^1$ is an unsubstituted or a substituted, straight or branched chain alkyl group having from 1 to about 20 carbon atoms, an unsubstituted or a substituted cycloalkyl group having from 3 to about 8 carbon atoms in the ring or an unsubstituted or a substituted aryl group;

$R^2$ is as defined for $R^1$ or is hydrogen;

$R^3$ is an unsubstituted or a substituted alkyl group having from 1 to about 24 carbon atoms, an unsubstituted or a substituted cycloalkyl group having from 3 to about 8 carbon atoms in the ring, an unsubstituted or a substituted aryl group having from 6 to about 24 carbon atoms or an unsubstituted or a substituted heterocyclic group having from 3 to about 8 atoms in the heterocyclic ring, wherein the hetero ring atoms can be nitrogen, oxygen, or sulfur;

with the proviso that when $R^3$ is a primary alkyl group, $R^1$ must contain at least 2 carbon atoms;

Q is oxo or —$NR^4$—;

$R^4$ is hydrogen; an unsubstituted or a substituted alkyl group having from 1 to about 24 carbon atoms; an unsubstituted or a substituted cycloalkyl group having from 3 to about 8 carbon atoms in the ring; or an unsubstituted or a substituted aryl group having from 6 to about 24 carbon atoms;

$R^5$ is an unsubstituted or a substituted linear or branched alkyl group having from 1 to about 32 carbon atoms;

n is 0 or 1; and

Z is hydrogen or a coupling off group, with the proviso that at least one of the $R^1$, $R^2$, $R^3$, $R^4$, $R^5$ or Z groups is of such size and configuration as to render the coupler compound substantially nondiffusible in the layer of a photographic recording material in which it is coated.

The specifically described combination in a phenolic coupler of (a) a sulfone or a modified sulfone-containing ballast group in the 5- position and a 2- position substituted alkylacylamino group provides couplers yielding high dye density while preserving other desirable dye properties. These results are surprising and could not have been predicted from the body of knowledge available before the investigations leading to this invention were carried out.

In preferred coupler compounds of this invention $R^1$ is alkyl having 1 to about 14 carbon atoms and $R^2$ is hydrogen. In particularly preferred coupler compounds $R^1$ is alkyl of 1 to about 4 carbon atoms and $R^2$ is hydrogen.

When the $R^3$, $R^4$ or $R^5$ groups are substituted such substituents may include alkyl, aryl, alkoxy, aryloxy, alkylthio, arylthio, hydroxy, halogen, alkoxycarbonyl, aryloxycarbonyl, carboxy, acyl, acyloxy, carbonamido, carbamoyl, alkylsulfonyl, arylsulfonyl, sulfonamido and sulfamoyl groups wherein the alkyl and aryl substituents, and the alkyl and aryl moieties of the alkoxy, aryloxy, alkylthio, arylthio, alkoxycarbonyl, arylcarbonyl, acyl, acyloxy, carbonamido, carbamoyl, alkylsulfonyl, arylsulfonyl, sulfonamido and sulfamoyl substituents can contain, respectively, from 1 to about 30 carbon atoms and from 6 to about 30 carbon atoms and can be further substituted with such substituents.

The $R^5$ alkyl groups can be substituted with one or more of halogen atoms, preferably chloro or fluoro, alkoxy groups, alkylthio groups, arylthio groups, alkylsulfonyl groups, arylsulfonyl groups, sulfonamido groups, acylamino groups, alkyloxycarbonyl groups, aryloxycarbonyl groups, carbamoyl groups, alkylcarbonyloxy groups, arylcarbonyloxy groups, carboxyl groups, cyano groups and hydroxyl groups.

Coupling off groups defined by Z are well known to those skilled in the art. Such groups can determine the equivalency of the coupler i.e., whether it is a 2-quivalent coupler or a 4-equivalent coupler. Such groups can also modify the reactivity of the coupler or can advantageously affect the layer in which the coupler is coated, or other layers in a photographic recording material, by performing, after release from the coupler, such functions as development inhibition, bleach inhibition, bleach acceleration and color correction.

Representative classes of coupling-off groups include alkoxy, aryloxy, heteroyloxy, sulfonyloxy, acyloxy, acyl, heterocyclyl, sulfonamido, phosphonyloxy and arylazo. These coupling-off groups are described in the art, for example, in U.S. Pat. Nos. 2,455,169, 3,227,551, 3,432,521, 3,476,563, 3,617,291, 3,880,661, 4,052,212 and 4,134,766; and in U. K. Patent and published application Nos. 1,466,728, 1,531,927, 1,533,039, 2,006,755A and 2,017,704A.

Examples of preferred coupling-off groups which can be represented by Z are:

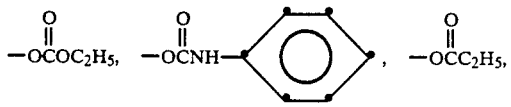

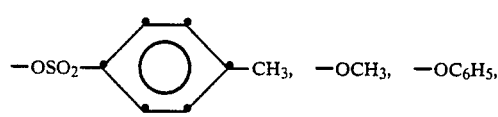

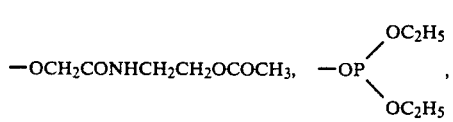

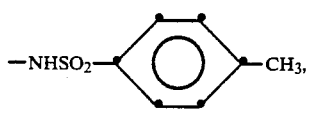

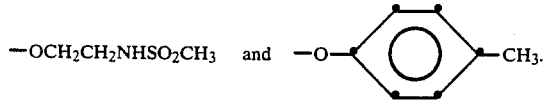

Especially preferred Z groups are hydrogen and

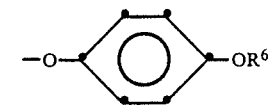

where $R^6$ is an alkyl or an alkoxy group having from 1 to about 10 carbon atoms, such as

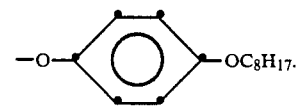

Specific coupler compounds of this invention are shown below in Table 1 with reference to the following structural formula:

TABLE 1

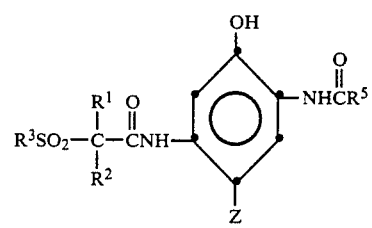

| Coupler Compound | $R^1$ | $R^2$ | $R^3$ | $R^5$ | Z* |
|---|---|---|---|---|---|
| 1 | $-C_{10}H_{23}$ | H | $-C_{18}H_{37}$ | $-C_3F_7$ | A |
| 2 | $-C_{14}H_{29}$ | H | $-CH_3$ | $-C_3F_7$ | H |
| 3 | $-C_{10}H_{21}$ | H | (thiophene) | $-C_3F_7$ | H |
| 4 | $-C_2H_5$ | H | $C_{16}H_{33}$ | $-C_3F_7$ | H |
| 5 | $-C_2H_5$ | H | $C_{16}H_{33}$ | $-CH_2CF_3$ | H |
| 6 | $-C_2H_5$ | H | $C_{16}H_{33}$ | $-CH_2CN$ | H |
| 7 | $-C_2H_5$ | H | $C_{16}H_{33}$ | $-CF_3$ | H |

Further specific coupler compounds useful in this invention are shown below in Table 2 with reference to the following structural formula:

TABLE 2

R³—QSO₂—C(R¹)(R²)—C(=O)—NH—[phenyl with OH, Z, NHC(=O)R⁵]

| Coupler Compound | R¹ | R² | R³ | Q | R⁵ | Z* |
|---|---|---|---|---|---|---|
| 8 | —C₁₄H₂₉ | H | —CH₃ | —O— | —C₃F₇ | A |
| 9 | —C₁₀H₂₁ | H | —NHSO₂—[phenyl-COOH] | —NH— | —C₃F₇ | H |
| 10 | —C₁₀H₂₁ | H | [phenyl-NHSO₂—phenyl-OH] | —NH— | —C₃F₇ | A |

*A = —O—[phenyl]—OCH₃

---

Coupler compounds of this invention can be prepared by reacting alkyl acid halides with an appropriate aminophenol, such as 2-amino-5-nitrophenol or 2-amino-4-chloro-5-nitro phenol to form the 2-carbonamido coupler moiety compounds. The nitro group can then be reduced to an amine and a separately prepared ballast moiety can be attached thereto by conventional procedures. Two-equivalent couplers can be prepared by known techniques, for example, by substitution of a 4-chloro group on the starting phenol. Details of such preparations are noted below relative to specific coupler compounds identified in Tables I and II.

SYNTHESIS EXAMPLE 1

Coupler Compound No. 4 was prepared as follows:

A. Preparation of phenolic coupler moiety:

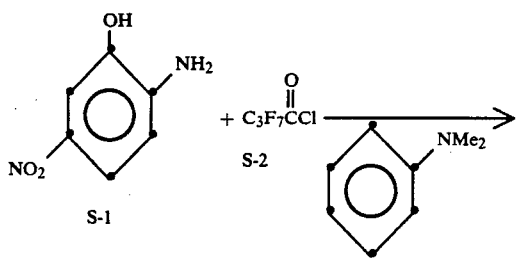

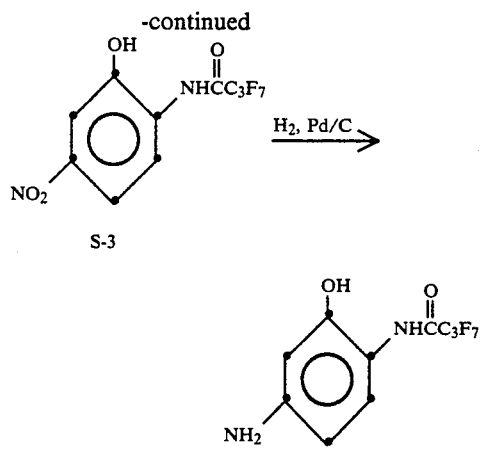

To a stirred solution of 30.8 g (0.20 mol) of 2-amino-5-nitro phenol (S-1) and 53.2 g (0.44 mole) of N,N-dimethylaniline in 500 ml ethyl acetate is added 51 g (0.22 mole) of heptafluoro butyryl chloride (S-2). After 3 hours stirring at ambient temperature, the reaction mixture is washed twice with 10% HCl, dried and concentrated to a solid. Crystallization from acetonitrile yielded 58.5 g of S-3.

A solution of 6 g (0.0171 mole) of nitro compound S-3 in 150 ml ethyl acetate was shaken for 3 hours with 1.5 g 10% palladium on carbon catalyst and 1 ml acetic acid under 276 kPa (40 lb) hydrogen pressure to provide the aminophenol S-4.

B. Preparation of the ballast acid chloride:

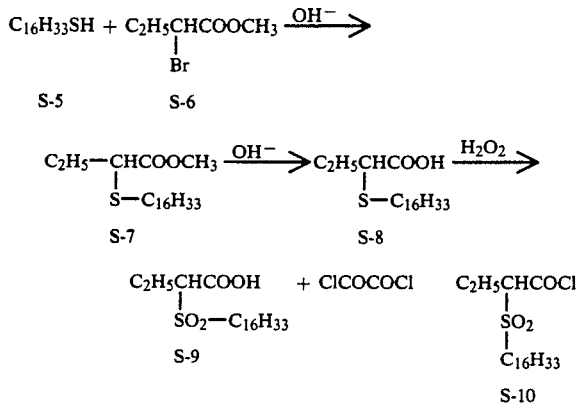

To a well stirred solution of 258.4 g (1 mol) n-hexadecyl mercaptan (S-5) and 217 g (1.2 mole) methyl alpha-bromobutyrate (S-6) in 500 ml ethanol was added, under nitrogen, a solution of 44 g (1.1 mol) sodium hydroxide in 300 ml water. After 1 hour a solution of 80 g (2 mol) sodium hydroxide in 1 liter tetrahydrofuran and 750 ml methanol was added and stirring continued 2 hours to hydrolyze the S-7 ester to the S-8 acid sodium salt. This salt, which precipitated on concentration of the reaction mixture, was suspended in 4.5 liters dilute hydrochloric acid and stirred 1 hour to yield 350 g moist white solid S-8 acid.

A solution of 1 g tungstic acid in aqueous sodium hydroxide was made slightly acidic by titration with acetic acid and then added at 30 degree C. to a solution of 290 g (0.84 mol) S-8 acid in 1.15 liter acetic acid. To this solution was added dropwise with stirring over a 30 minute period 210 g (1.85 mole) of 30% hydrogen peroxide solution. After 2 hours additional stirring while heating with a steam bath, the reaction mixture was allowed to cool to 30 degree C. and a white crystalline product was isolated by filtration. Washing with ligroin and acetonitrile yielded 233 g S-9 acid.

7.1 g (0.0188 mol) of the S-9 acid in 150 ml dichloromethane was treated with 3.2 ml (0.0377 mole) oxalyl chloride and 10 drops dimethylformamide, stirred for 1.5 hours, and concentrated to yield 7.3 g ballast acid chloride S-10 as white solid.

C. Synthesis of Coupler Compound No. 4:

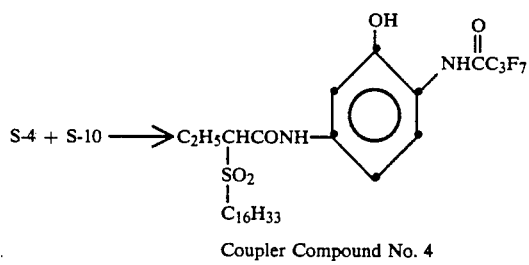

Coupler Compound No. 4

To a stirred solution of 5.5 g (0.0171 mole) of the S-4 amine and 6.2 g (0.0543 mole) N,N-dimethylaniline in 300 ml ethyl acetate is added 7.3 g (0.01885 mole) of S-10 ballast acid chloride. After stirring for 1 hour, the reaction mixture is washed three times with 10% HCl, dried and concentrated to a solid. Crystallization from acetonitrile gave 10.8 g white solid. Mass spec and elemental analysis confirm product structure as that of Coupler Compound No. 4.

The cyan dye-forming couplers of this invention can be used in the ways and for the purposes that cyan dye-forming couplers are used in the photographic art. Typically, the couplers are incorporated in silver halide emulsions and the emulsions coated on a support to form a photographic element. Alternatively, the couplers can be incorporated in photographic elements adjacent the silver halide emulsion where, during development, the coupler will be in reactive association with development products such as oxidized color developing agent.

The cyan dye-forming couplers described herein can be combined with development inhibitor releasing compounds having the structure:

$$\begin{array}{c} CAR \\ | \\ TIME \\ | \\ INH \end{array}$$

where CAR is a carrier moiety, TIME is a timing group and INH is a development inhibitor moiety. Such combination enhances the sharpness of cyan images obtained from the described couplers.

The INH development inhibitor moiety is more fully described in co-pending U.S. Pat. application Ser. No. 213,415 filed Jun. 30, 1988.

As used herein, the term "in reactive association" signifies that the coupler is in the silver halide emulsion layer or in an adjacent location where, during processing, it is capable of reacting with silver halide development products.

The photographic elements can be either single color or multicolor elements. In a multicolor element, the cyan dye-forming coupler of this invention is usually associated with a red-sensitive emulsion, although it could be associated with an unsensitized emulsion or an emulsion sensitized to a different region of the spectrum. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising of at least one red-sensitive silver halide emulsion layer having associated therewith at least one cyan dye-forming coupler, at least one of the cyan dye-forming couplers being a coupler of this invention, a magenta dye image-forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the elements of this invention, reference will be made to Research Disclosure, December 1978, Item 17643, published by Kenneth Mason Publications, Ltd., The Old Harbourmaster's, 8 North Street, Emsworth, Hampshire PO10 7DD, ENGLAND. This publication will be identified hereafter by the term "Research Disclosure."

The silver halide emulsions employed in the elements of this invention can be either negative-working or positive-working. Suitable emulsions and their preparation are described in Research Disclosure Section I and II and the publications cited therein. Tabular photographic silver halide grains are also useful. Such tabular grain silver halide is described in, for example, U.S. Pat. No. 4,434,226 and in *Research Disclosure*, January 1983, Item No. 22534. Suitable vehicles for the emulsion layers and other layers of elements of this invention are described in Research Disclosure Item 17643, Section IX and the publications cited therein.

In addition to the couplers described herein the elements of this invention can include additional couplers as described in Research Disclosure Section VII, paragraphs D, E, F and G and the publications cited therein. These additional couplers can be incorporated as described in Research Disclosure Section VII, paragraph C and the publications cited therein.

The photographic elements of this invention can contain brighteners (Research Disclosure Section V), antifoggants and stabilizers (Research Disclosure Section IV), antistain agents and image dye stabilizers (Research Disclosure Section VII, paragraphs I and J), light absorbing and scattering materials (Research Disclosure Section VIII), hardeners (Research Disclosure Section XI), plasticizers and lubricants (Research Disclosure Section XII), antistatic agents (Research Disclosure Section XIII), matting agents (Research Disclosure Section XVI) and development modifiers (Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

Preferred color developing agents ae p-phenylene diamines. Especially preferred are 4-amino-3-methyl-N,N-diethylaniline hydrochloride, 4-amino-3-methyl-N-ethyl-N-β-(methanesulfonamido)-ethylaniline sulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N-(2-methoxy-ethyl)-m-toluidine di-p-toluene sulfonic acid.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing to remove silver and silver halide, washing and drying.

In the following examples, a measure of each coupler's coupling effectiveness is represented by G which is the ratio of its photographic dye image gamma (the slope of the sensitometric curve) to that of the analogous nonsulfone Control Coupler. Such normalization of the data compensates for coating and processing variations by relating the performance of each test coupler as described herein to that of a control coupler coated and processed at the same time and in the same manner.

Processing and testing procedures were kept constant. Particularly useful couplers provided dye images with $G > 1.00$, and Dmax > Dmax of the control.

EXAMPLE 1

Dispersions of a coupler of the invention (4), Comparative Coupler C and respective analogous nonsulfone control couplers (A) and (B) were prepared. The coupler solvent dibutyl phthalate was used at a 1:0.5 coupler: coupler solvent weight ratio. Each coupler was coated at 0.15 mmoles/ft$^2$ with 84 mg/ft$^2$ of silver as a medium-large grain, polydisperse AgBrI (6.5 mole % I) emulsion. The coatings were exposed and subjected to an E-6 process with and without citrazinic acid (CZA) in the color developer at 0.57 g/l. Results are shown below:

| Coupler | G (with CZA) | G (no CZA) | Dmax (with CZA) | Dmax (no CZA) | λmax (nm) |
|---|---|---|---|---|---|
| A (Control) | 1.00 | 1.00 | 1.54 | 2.02 | 656 |
| 4 | 1.68 | 1.32 | 2.64 | 3.24 | 646 |
| B (Control) | 1.00 | 1.00 | 2.68 | 3.34 | 641 |
| C (Comparative Example) | .11 | .50 | 1.04 | 1.29 | 622 |

It is evident that the use of a sulfone-containing ballast dramatically improves G values and Dmax values for the 2-alkylcarbonamido coupler, 4, but leads to inferior G and Dmax values for the comparative 2-arylcarbonamido Coupler, C.

Control Coupler A

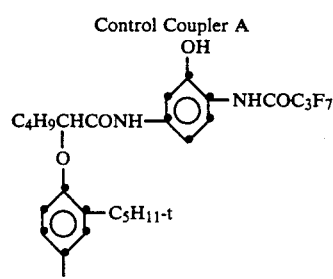

Control Coupler B

-continued

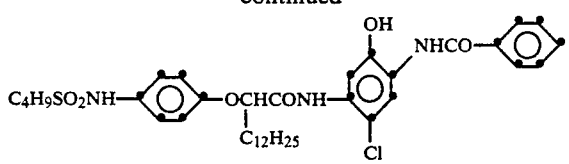

Comparative Coupler C

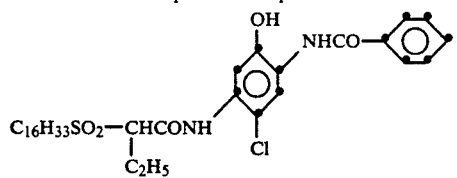

This invention has been described in detail with particular reference to preferred embodiments thereof, but it will be understood that variations and modifications can be effected within the spirit and scope of the invention.

What is claimed is:

1. A photographic recording material comprising a support and a photosensitive silver halide emulsion which has associated therewith a cyan dye-forming coupler compound having the structural formula:

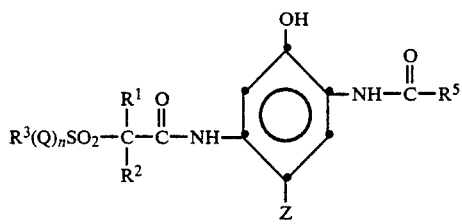

wherein:
$R^1$ is an unsubstituted or a substituted, straight or branched chain alkyl group having from 1 to about 20 carbon atoms, an unsubstituted or a substituted cycloalkyl group having from 3 to about 8 carbon atoms in the ring or an unsubstituted or a substituted aryl group;
$R^2$ is as defined for $R^1$ or is hydrogen;
$R^3$ is an unsubstituted or a substituted alkyl group having from 1 to about 24 carbon atoms, an unsubstituted or substituted cycloalkyl group having from 3 to about 8 carbon atoms in the ring, an unsubstituted or a substituted aryl group having from 6 to about 24 carbon atoms or an unsubstituted or a substituted heterocyclic group having from 3 to about 8 atoms in the heterocyclic ring, wherein the hetero ring atoms can be nitrogen, oxygen, or sulfur;
with the proviso that when $R^3$ is a primary alkyl group $R^1$ must contain at least 2 carbon atoms;
Q is —O— or —$NR^4$—;
$R^4$ is hydrogen; an unsubstituted or a substituted alkyl group having from 1 to about 24 carbon atoms; and unsubstituted or a substituted cycloalkyl group having from 3 to about 8 carbon atoms in the ring; or an unsubstituted or a substituted aryl group having from 6 to about 24 carbon atoms;
$R^5$ is an unsubstituted or a substituted linear or branched chain alkyl group having from 1 to about 32 carbon atoms;
n is 0 or 1; and
Z is hydrogen or a coupling off group;
with the proviso that at least one of the $R^1$, $R^2$, $R^3$, $R^4$, $R^5$ or Z groups is of such size and configuration as to render the coupler compound substantially nondiffusible in the layer of the photographic recording material in which it is coated.

2. The photographic material of claim 1 wherein Q is —$NR^4$—.

3. The photographic element of claim 1 wherein Q is —O—.

4. The photographic element of claim 1 wherein $R^1$ is alkyl of from 1 to about 14 carbon atoms and $R^2$ is hydrogen.

5. The photographic material of claim 4 wherein $R^1$ is alkyl of from 1 to about 4 carbon atoms and $R^2$ is hydrogen.

6. The photographic material of claim 2 wherein $R^4$ is hydrogen.

7. The photographic material of claim 1 wherein $R^5$ is an alkyl group substituted with one or more halogen atoms.

8. The photographic material of claim 1 wherein Z is hydrogen or

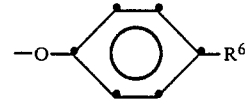

where $R^6$ is an alkyl or an alkoxy group having from 1 to about 10 carbon atoms.

9. The photographic material of claim 1 wherein the cyan dye-forming coupler compound has the structural formula:

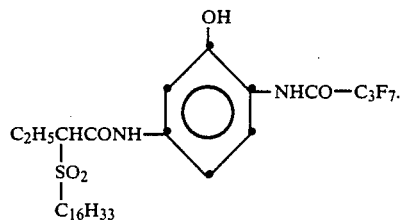

* * * * *